United States Patent
Graumann

(10) Patent No.: US 9,532,764 B2
(45) Date of Patent: Jan. 3, 2017

(54) ARRANGEMENT AND METHOD FOR IMAGE COMBINATION

(75) Inventor: Rainer Graumann, Hoechstadt (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 56 days.

(21) Appl. No.: 14/348,148

(22) PCT Filed: Sep. 3, 2012

(86) PCT No.: PCT/EP2012/067135
§ 371 (c)(1),
(2), (4) Date: Mar. 28, 2014

(87) PCT Pub. No.: WO2013/045221
PCT Pub. Date: Apr. 4, 2013

(65) Prior Publication Data
US 2014/0247925 A1 Sep. 4, 2014

(30) Foreign Application Priority Data

Sep. 28, 2011 (DE) .......................... 10 2011 083 632

(51) Int. Cl.
*A61B 6/00* (2006.01)
*A61B 6/12* (2006.01)

(52) U.S. Cl.
CPC ................. *A61B 6/583* (2013.01); *A61B 6/12* (2013.01); *A61B 6/5235* (2013.01); *A61B 6/4266* (2013.01); *A61B 6/4423* (2013.01); *A61B 2090/364* (2016.02); *A61B 2090/3966* (2016.02)

(58) Field of Classification Search
CPC .............................. A61B 6/463; A61B 6/5241
USPC .......................................................... 378/207
See application file for complete search history.

(56) References Cited

U.S. PATENT DOCUMENTS

| 5,409,004 | A | 4/1995 | Sloan | |
|---|---|---|---|---|
| 6,658,089 | B1 * | 12/2003 | Mohr | ..................... G01N 23/04 378/162 |
| 2003/0130576 | A1 | 7/2003 | Seeley et al. | |
| 2005/0094771 | A1 * | 5/2005 | Basu | ...................... A61B 6/583 378/207 |
| 2006/0219926 | A1 | 10/2006 | Shoji et al. | |
| 2009/0028291 | A1 | 1/2009 | Graumann | |
| 2009/0238341 | A1 * | 9/2009 | Kawamura | .............. A61B 6/04 378/162 |
| 2009/0245464 | A1 * | 10/2009 | Yamaguchi | .......... A61B 6/5241 378/62 |

FOREIGN PATENT DOCUMENTS

| DE | 1895848 U | 7/1964 |
|---|---|---|
| DE | 102007025448 A1 | 12/2008 |
| DE | 102010023036 A1 | 12/2011 |

* cited by examiner

*Primary Examiner* — Hoon Song
(74) *Attorney, Agent, or Firm* — Laurence Greenberg; Werner Stemer; Ralph Locher

(57) ABSTRACT

It is possible, by use of a calibration scale shown in partial X-ray images, for non-overlapping partial X-ray images to be combined and assigned to one another. Therefore the individual x-ray images which are not overlapping can be related spatially. In this manner x-ray images only have to be made of surgically significant regions and therefore the x-ray exposure of a patient is reduced.

11 Claims, 4 Drawing Sheets

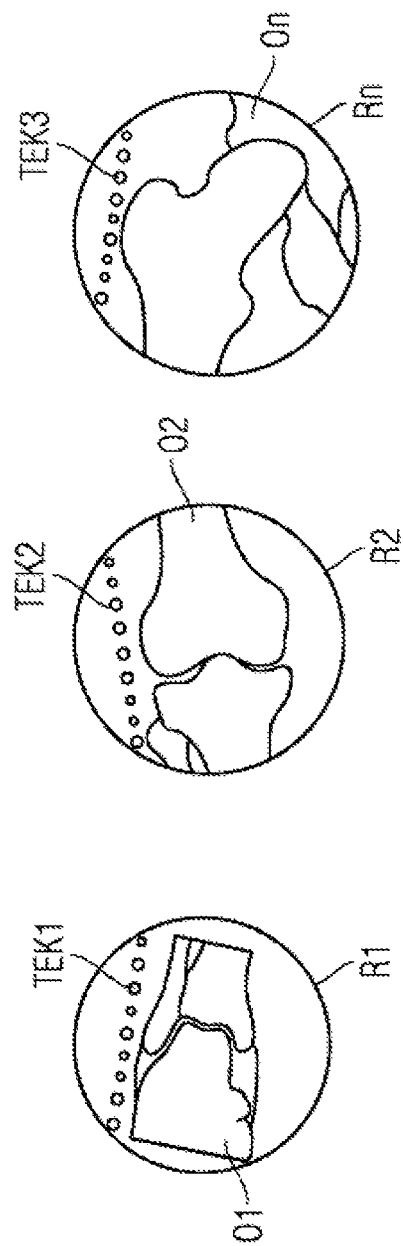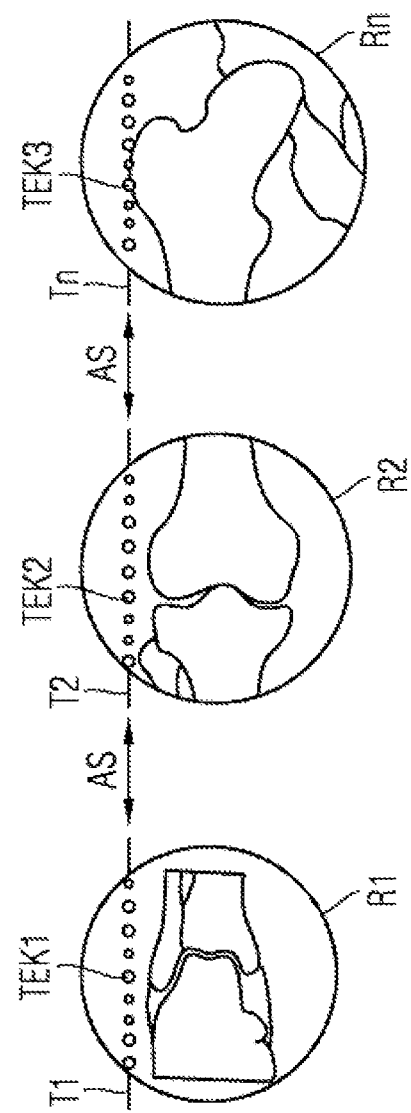

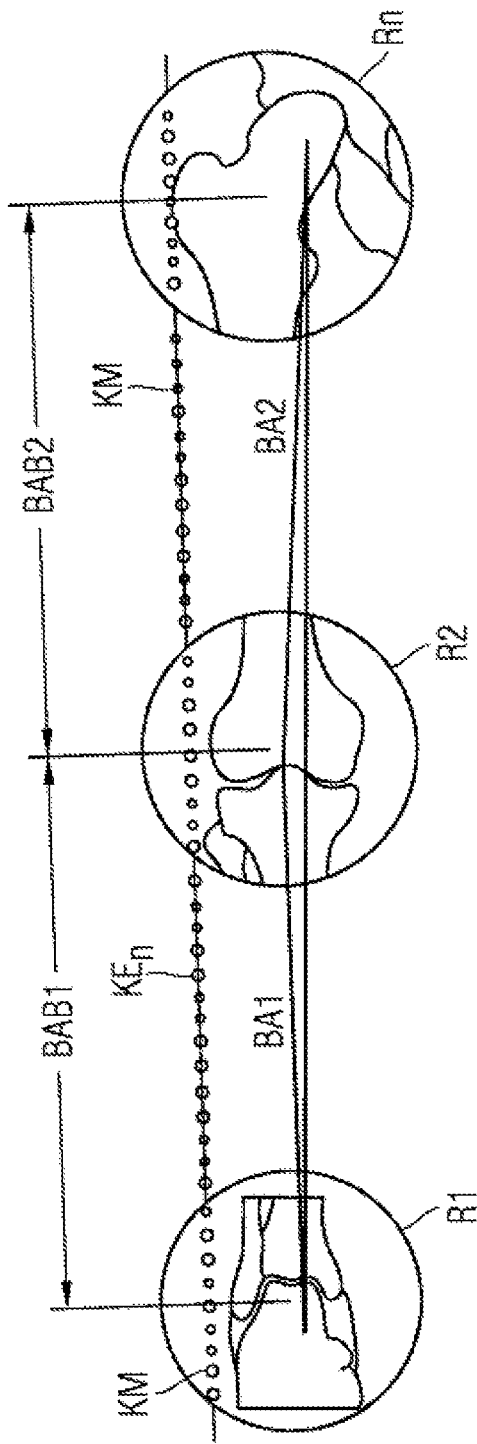

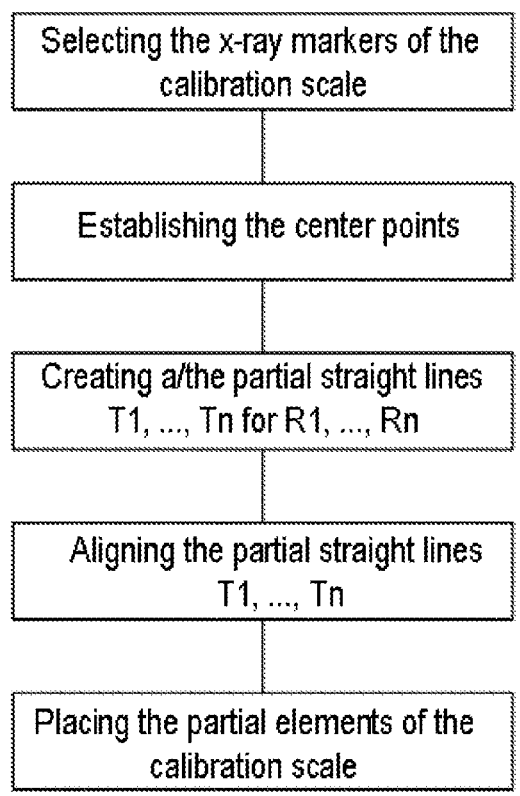
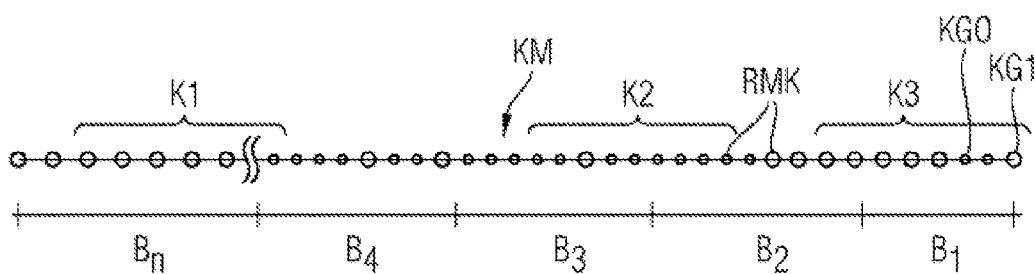

ARRANGEMENT AND METHOD FOR IMAGE COMBINATION

BACKGROUND OF THE INVENTION

Field of the Invention

The invention relates to an arrangement and a method, in particular for combining x-ray images.

Due to a restricted number of image sizes in x-ray detector units, there is often the need to make a plurality of x-ray images, for example of different regions of a body part, for a diagnosis, a pre-surgical preliminary discussion or an intra-operative progress or quality control. An example of this could be the recording of a leg. To this end, the individual x-ray recordings have to have a large-scale overlap in order to be able to relate the x-ray recordings to one another. Then position probabilities of prominent points or structures are calculated in the overlapping regions, wherein these regions have been assumed not to have a parallax. However, this harbors the disadvantage of increased x-ray exposure and high computational outlay. In the case of a multiplicity of x-ray images to be related to one another, a relation is formed on the basis of a correlation method since there are only a few prominent structures or features in the overlapping regions of the x-ray images.

BRIEF SUMMARY OF THE INVENTION

The invention is based on the object of specifying a further arrangement and an associated method for combining x-ray images.

The object is achieved by the features specified in the patent claims.

A device for aligning, joining together or merging x-ray images is proposed, which makes use of at least one calibration scale, formed from at least a first type of x-ray markers, wherein this calibration scale is also imaged at least in part in the x-ray images to be joined together or related to one another.

In the associated method, at least one calibration scale, formed from at least a first type of x-ray markers, is imaged at least in part in x-ray images to be joined to one another, wherein the locality of the selected x-ray markers in the respective x-ray image is established on the basis of an electronically stored characteristic of the calibration scale.

The invention harbors the advantage that individual x-ray images, which for example are not overlapping, can be related spatially.

The invention harbors the advantage that x-ray images only have to be made of surgically significant regions and so the x-ray exposure of a patient is thus reduced further.

The invention harbors the advantage that the individual x-ray images can be aligned to one another, both along an axis connecting these and also at the distances there between.

The invention harbors the advantage that the x-ray images can be aligned to one another in a simple manner.

The invention harbors the advantage that, as a result of sterile packaging, the calibration scale ensures a sterile environment on the operating table during a surgical intervention. The invention harbors the advantage that the calibration scale can be integrated into the operating table.

The invention harbors the advantage that the calibration scale can be aligned parallel to the leg.

The invention harbors the advantage that the incline of the calibration scale to a reference plane, e.g. the floor of the operating theater, can be calculated by the size of the imaged marker/marker spheres of the calibration scale in the case of, for example, a non-parallel alignment of the leg to said reference plane.

The invention harbors the advantage that, if spheres are used as marker elements, any orientations of the calibration scale can be detected in the recordings.

The invention will be explained in more detail by means of a depicted exemplary embodiment.

BRIEF DESCRIPTION OF THE SEVERAL VIEWS OF THE DRAWING

FIG. 1 shows individual x-ray images with marker elements of a calibration scale, FIG. 2 shows an alignment of the x-ray images, FIG. 3 shows a local and axial alignment of the x-ray images, FIG. 4 shows a flowchart, FIG. 5 shows a calibration scale and FIG. 6 shows a data processing unit.

DESCRIPTION OF THE INVENTION

Figure 6:
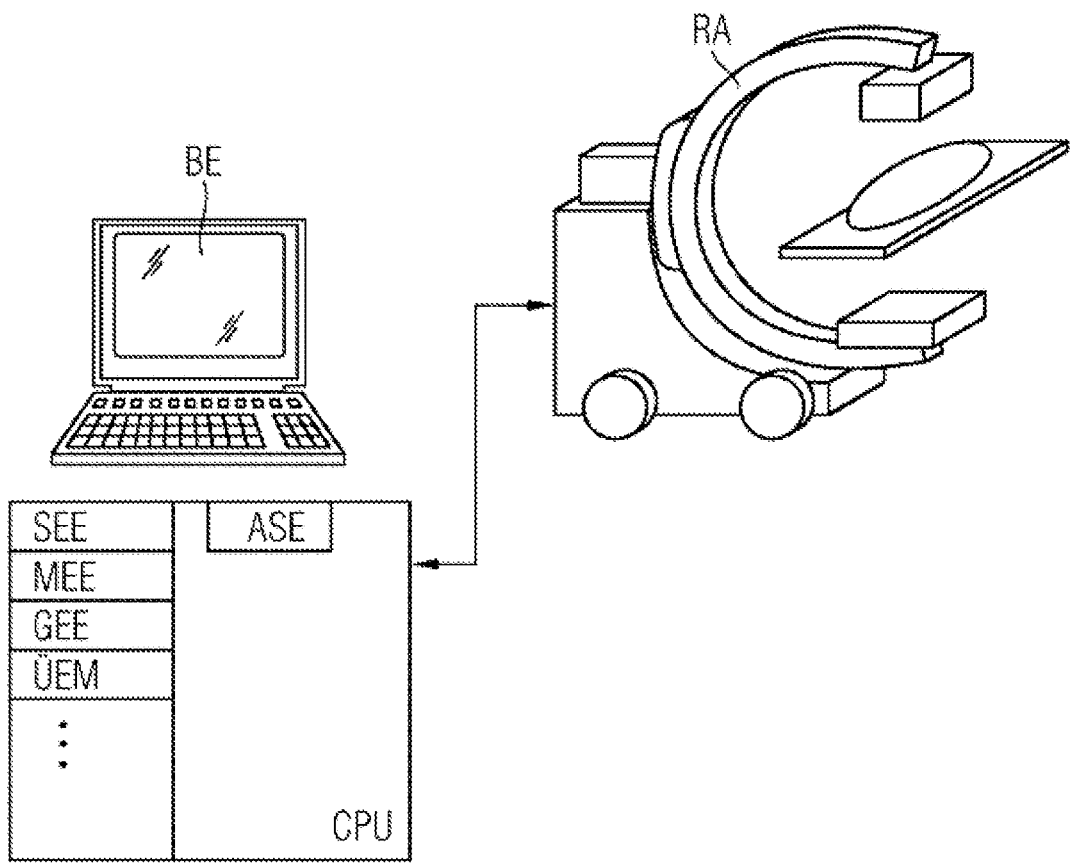

By means of this arrangement and the associated method, it is possible, by means of a calibration scale imaged in the partial x-ray images, to combine and align even non-overlapping partial x-ray images, or these can be related to one another.

FIG. 1 depicts three x-ray images R1, R2, . . . , Rn of a body part, e.g. a leg, in an exemplary manner. These x-ray images can also be referred to as partial x-ray images. The shown x-ray images R1, R2, . . . , Rn can be imaged on a monitor unit DE of a data processing installation DVE provided to an x-ray installation RA. The first x-ray image R1 depicts the ankle joint O1, the second x-ray image R2 depicts the knee joint O2 and the third x-ray image Rn depicts the upper region of the femur ON. During the x-ray recordings R1, R2, . . . , Rn, a calibration scale KM, as is depicted e.g. in FIG. 5, is placed directly on the leg of the patient. Here, the calibration scale KM is placed in such a way that the latter, at least in sections, is also imaged in the individual x-ray images R1, . . . , Rn. A first part of the calibration scale TEK1 with a first calibration code K1 is depicted in the first x-ray image R1. A second partial element of the calibration scale TEK2 with a second calibration code K2 is depicted in the second x-ray image R2 and a third partial element of the calibration scale TEK3 with a third calibration code K3 is depicted in the third x-ray image Rn.

In one embodiment, the calibration scale can be integrated into the operating table.

In a further embodiment, the calibration scale can be packaged in a sterile manner and arranged in the vicinity of the surgical intervention region.

In FIG. 2, the individual x-ray images R1, R2 and Rn are depicted aligned to one another. The x-ray images are aligned by virtue of the x-ray markers of the calibration scale KM being selected and the center points thereof being established. These center points are connected to one another. The straight line in the respective x-ray image forms a partial straight line T from the calibration scale KM. From the size of the spheres in the x-ray images, information in respect of the depth of the individual images also can be additionally calculated.

In this example, a first, second and n-th partial straight line T1, T2 and Tn are formed. The first, second and n-th x-ray image R1, R2 and Rn are aligned on the basis of the first, second and n-th partial straight lines T1, T2, Tn along an alignment axis AS.

In FIG. 3, the actual distance between the individual partial sections on the calibration scale KM is also taken into account in addition to the alignment along the alignment axis AS. Thus, it is possible to set, in addition to the alignment of the individual x-ray images R1, R2, . . . , Rn, also the local alignment thereof in relation to the calibration scale KM as a result of the spherical elements KEn arranged in the calibration scale KM. The local arrangement of the respective partial straight lines T1, T2, . . . , Tn is brought about on the basis of the coding K1, K2, K3 respectively assigned thereto. The coding is available with the coding scale KM, as shown in FIG. 5. By way of example, the coding can be achieved by an arrangement of x-ray marker spheres RMK with different diameters. After the first, second and n-th x-ray image R1, R2 and Rn is locally determined on the basis of the coding of the calibration scale KM, it is possible to establish a first and second image spacing BAB1, BAB2. By marking anatomical points, which for example set a leg axis, in the x-ray images, it is possible to determine a first leg axis BA1 and a second leg axis BA2. FIG. 4 schematically reproduces a flowchart with method steps for the local alignment of x-ray images using a calibration scale.

In a first method step, the x-ray marker spheres, imaged in the x-ray images, of the calibration scale KM are selected using a selection unit SEE.

In a subsequent processing step, the center point of individual x-ray marker spheres is established using a center-point establishment unit MEE.

In the third processing step, a straight-line formation unit GEE connects the center points of the individual x-ray marker spheres in each x-ray image to one another and forms a partial straight line there from.

In the fourth processing step, the partial straight lines are aligned to one another on an alignment axis AS by means of an alignment unit ASE.

In a final method step, the exact placement of the respective partial straight lines T1, T2, Tn is established in a correspondence module OEM on the basis of the partial calibration code K1, K2, Kn of the calibration scale KM. A local placement of the different x-ray marker spheres on the partial straight lines T1, T2, Tn is brought about on the basis of a correspondence of the x-ray marker spheres RMK arranged on the calibration scale KM.

The x-ray recordings R1, R2, Rn shown in FIGS. 1 to 3 are x-ray images which were recorded from the same direction. A further application with the calibration scale KM described here is likewise possible, in which image sequences were acquired from different perspectives. In so doing, the alignment of the x-ray images from the different perspectives can be brought about according to the sequence described below.

If the scale remains fixed during the change in the viewing direction, this method can additionally also derive 3D information. In order to obtain 3D information from two different viewing directions, use can be made of two calibration scales, which are optionally arranged parallel to one another with a small spacing there between. Proceeding from the x-ray source, it is then necessary to establish in each case the angles to the individual calibration scales.

FIG. 5 shows a calibration scale KM. It consists of a first and second type of spherical x-ray marker RMK, which markers are arranged on a radiolucent material, for example a plastic. The center points of the x-ray marker spheres lie on a straight line. In this embodiment, first and second x-ray marker spheres KG1, KG0 with two different diameters are used as radio paque spheres. Instead of the different diameters, the x-ray spheres can have different x-ray absorptions. The different spheres are arranged next to one another corresponding to a digital notation with a binary code. The first sphere KG1 with a first diameter corresponds to a 1 for a first bit of a byte B1. The second sphere KG0 corresponds to a second bit, occupied with 0, of a byte B1. It is then possible to arrange a first byte, starting at a first end of the calibration scale KM. In addition to a sphere sequence corresponding to sequence of bytes B1, B2, . . . , Bn with equidistant spacing, the x-ray marker spheres of the calibration scale can additionally have different distances from one another. In a further embodiment, the same and/or different x-ray marker spheres can be arranged with the same and/or changing distances on a bar. The x-ray marker spheres can also have such a design that these have different x-ray absorptions while having approximately the same diameter.

The locality of the selected x-ray markers RMK of the respective x-ray image can be determined on the basis of an electronically stored characteristic of the coding scale KM.

FIG. 6 schematically depicts a data processing unit DVE assigned to an x-ray installation RA. In said data processing unit, the modules, as listed in FIG. 4, can be arranged.

If no data processing installation is provided, the calibration scale can be arranged as a transparent film image on a light box. The sequence of x-ray markers TEK1, TEK2, . . . , TEKn from the individual x-ray images R1, R2, . . . , Rn is then brought into correspondence with the respective section K1, K2, . . . , K3 on the calibration scale KM.

LIST OF REFERENCE SIGNS

RA X-ray installation
DVE Data processing installation
BE Monitor unit
SEE Selection unit
MEE Center-point establishment unit
GEE Straight-line formation unit
ÜEM Correspondence module
CPU Central processing unit
ASE Alignment unit
R1 First x-ray image
R2 Second x-ray image
Rn n-th x-ray image
O2 Second object
On n-th object
AS Alignment axis
KEn Spherical elements
K1 First calibration code
K2 Second calibration code
K3 Third calibration code
TEK1 First partial element of the calibration scale
TEK2 Second partial element of the calibration scale
TEK3 Third partial element of the calibration scale
BA1 First leg axis
BA2 Second leg axis
BAB1 First image spacing
BAB2 Second image spacing
KM Calibration scale
KG1 First x-ray marker sphere
KG0 Second x-ray marker sphere
B1 First byte
B2 Second byte Bn n-th byte
T1 First partial straight line
T2 Second partial straight line
Tn n-th partial straight line
RMK X-ray marker Patent

The invention claimed is:

1. An apparatus for aligning x-ray images, the apparatus comprising:
 a linear calibration device having at least one type of spherically shaped X-ray markers being included in the X-ray images to be associated with each other, said spherically shaped X-ray markers including at least a first type of x-ray markers and a second type of x-ray markers having a different diameter than said first type of x-ray markers, wherein said first and second type x-ray markers are disposed according to a coding; and
 a correspondence module for establishing a locality of selected ones of said spherically shaped x-ray markers, wherein the locality is established by correspondence of respective partial sections on a basis of an electronically recallable characteristic of said linear calibration device.

2. The apparatus according to claim 1, wherein said linear calibration device has a linear design.

3. The apparatus according to claim 1, wherein distances between said first and/or second type x-ray markers are identical.

4. The apparatus according to claim 1, wherein said spherically shaped x-ray markers have different x-ray absorptions.

5. The apparatus according to claim 1, wherein each individual one of said spherically shaped x-ray markers correspond to one bit of a binary sequence.

6. The apparatus according to claim 1, further comprising a selection unit for selecting said spherically shaped x-ray markers.

7. The apparatus according to claim 1, further comprising a center-point establishment unit for determining center points of selected ones of said spherically shaped x-ray markers.

8. The apparatus according to claim 1, further comprising a straight-line formation unit, wherein a partial straight line is formed in each x-ray image using at least two center points of selected ones of said spherically shaped x-ray markers.

9. The apparatus according to claim 8, further comprising an alignment unit, wherein the partial straight line is aligned on a basis of an alignment axis.

10. A method for aligning x-ray images, which comprises steps of:
 placing at least one calibration scale on or next to a part of a patient being imaged; and
 imaging the calibration scale in conjunction with the part of the patient, the calibration scale having spherically shaped X-ray markers including a first type of x-ray markers and a second type of x-ray markers having a different diameter than the first type of x-ray markers, the calibration scale being imaged with the spherically shaped X-ray markers in each of the X-ray images, the first and second type x-ray markers are disposed according to a coding;
 taking a plurality of the x-ray images of the part of the user resulting in the x-ray images pertaining to different regions of the part of the user; and
 aligning the plurality of the x-ray images into a larger x-ray image, an alignment of the x-ray images with each other being dependent on a calibration scale portion imaged in each x-ray image.

11. The method according to claim 10, which further comprises establishing a locality of selected ones of the spherically shaped x-ray markers in the x-ray images on a basis of an electronically stored characteristic of the calibration scale.

* * * * *